United States Patent [19]

Truener et al.

[11] 4,189,482
[45] Feb. 19, 1980

[54] PENICILLINS HAVING AN IMINO SUBSTITUTED PIPERAZINDIONCARBONYLAMINO ACYL SIDECHAIN

[75] Inventors: Uwe D. Truener; Hermann Breuer, both of Regensburg, Fed. Rep. of Germany

[73] Assignee: E. R. Squibb & Sons, Inc., Princeton, N.J.

[21] Appl. No.: 950,916

[22] Filed: Oct. 12, 1978

[51] Int. Cl.² .................. A61K 31/43; C07D 499/64; C07D 499/66; C07D 499/68
[52] U.S. Cl. .................... 424/250; 424/271; 260/239.1
[58] Field of Search ........... 260/239.1; 424/271, 424/250

[56] References Cited

U.S. PATENT DOCUMENTS 4,087,424  5/1978  Saikawa et al. ............... 260/239.1

FOREIGN PATENT DOCUMENTS 836022  5/1976  Belgium ............................ 260/239.1

Primary Examiner—Gerald A. Schwartz
Attorney, Agent, or Firm—Lawrence S. Levinson; Stephen B. Davis

[57] ABSTRACT

Penicillins of the formula

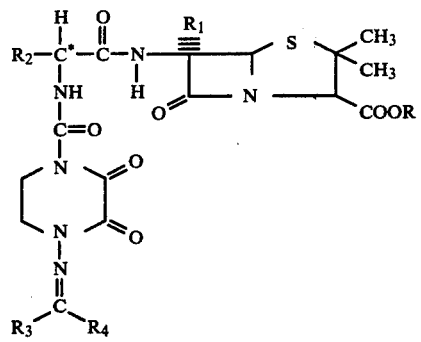

wherein R is hydrogen, sodium, potassium or certain ester groups; $R_1$ is in the α-configuration and is hydrogen or methoxy; $R_2$ is hydrogen, lower aklkyl, cycloalkyl, cycloalkenyl, cycloalkadienyl, substituted or unsubstituted phenyl, benzyl, phenethyl, thienyl, furyl, or pyridyl, or 2-amino-4-thiazolyl; $R_3$ is lower alkyl or substituted or unsubstituted phenyl, benzyl, phenethyl, thienyl or furyl; and $R_4$ is hydrogen or lower alkyl; are disclosed. These compounds possess useful antibacterial activity.

8 Claims, No Drawings

PENICILLINS HAVING AN IMINO SUBSTITUTED PIPERAZINDIONCARBONYLAMINO ACYL SIDECHAIN

BACKGROUND OF THE INVENTION

Saikawa et al. in U.S. Pat. No. 4,087,424 disclose penicillin and cephalosporin compounds having a substituted piperazindioncarbonylamino acyl sidechain. Penicillins having an (N-alkyl or other substituted piperazindioncarbonylamino) substituent on the 2-position carbon atom of a phenylacetamido sidechain are specifically disclosed as compounds 36–59.

Bayer in Belgian Pat. No. 836,022 disclose penicillin and cephalosporin compounds having an imino substituted imidazoledioncarbonylamino group at the 2-position carbon atom of a phenylacetamido, cyclohexenylacetamido, or cyclohexadienylacetamido acyl sidechain.

SUMMARY OF THE INVENTION

This invention is directed to penicillins of the formula:

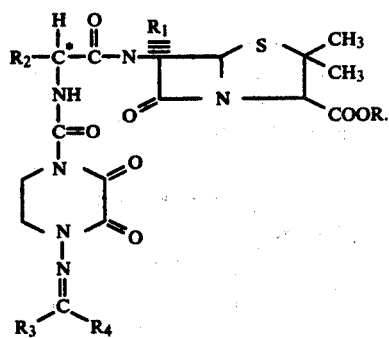

R represents hydrogen, sodium, potassium, t-butyl, benzyl, p-methoxybenzyl, p-nitrobenzyl, diphenylmethyl, 2,2,2-trichloroethyl, trimethylsilyl, —CH₂—O—lower alkyl,

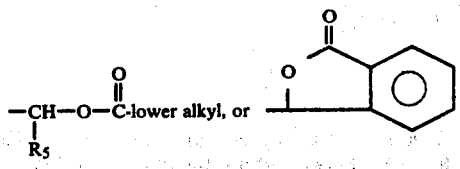

$R_1$ is in the α-configuration and is hydrogen or methoxy.

$R_2$ represents hydrogen, lower alkyl, cycloalkyl, cycloalkenyl, cycloalkadienyl,

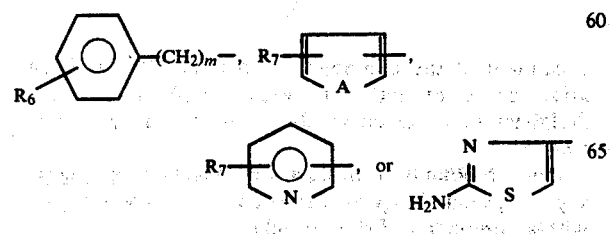

wherein $R_6$ is hydrogen, methyl, ethyl, methoxy, ethoxy, hydroxy, Cl, or Br; m is zero, 1 or 2; A is O or S; and $R_7$ is hydrogen, methyl, ethyl, Cl or Br.

$R_3$ represents lower alkyl,

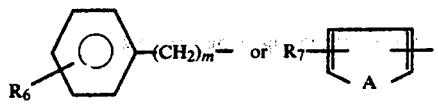

wherein $R_6$, $R_7$, m and A are as defined above.

$R_4$ represents hydrogen or lower alkyl.

$R_5$ represents hydrogen or lower alkyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbons containing 1 to 4 carbons, e.g. methyl, ethyl, i-propyl, t-butyl, etc.

Cycloalkyl refers to groups having 3 to 7 carbons in the ring, i.e. cyclopropyl, cyclobutyl, cyclopentyl, cyclohexyl, and cycloheptyl. The term cycloalkenyl represent rings having 5 to 7 carbons with one double bond, i.e. cyclopentenyl, cyclohexenyl, etc. The term cycloalkadienyl represents a ring having 6 or 7 carbons with two double bonds located at various positions such as 1,4-cyclohexadienyl which is preferred.

The compounds of formula I can be prepared by several methods. For example, an α-amino compound of the formula

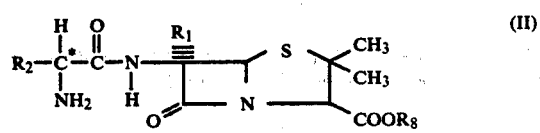

wherein $R_8$ is hydrogen or a readily removable ester group such as trimethylsilyl, 2,2,2-trichloroethyl, diphenylmethyl, benzyl, substituted benzyl, or t-butyl and $R_1$ is hydrogen or methoxy, can be reacted with an acid chloride of the formula

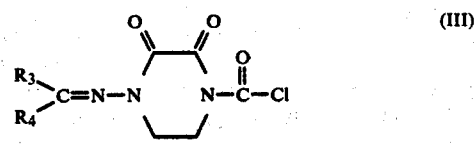

to yield the corresponding compound of formula I. When $R_8$ is an ester group, this group can be removed according to known methods to yield the corresponding free acid compound.

The α-amino intermediate of formula II can be prepared by various means such as by acylating a 6-amino penicillin of the formula

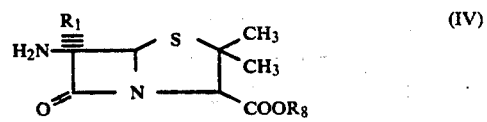

with a substituted α-amino acid of

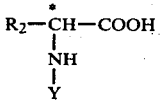
(V)

wherein Y is a protecting group such as

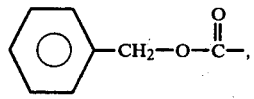

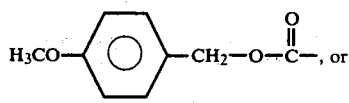, or

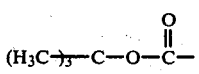

and then removing the α-amino protecting group.

The α-amino penicillins of formula II are taught in various patents. For example, the compounds wherein $R_1$ is hydrogen are taught in U.S. Pat. Nos. 2,985,648; 3,192,198; 3,278,525; 3,316,247; 3,342,677; 3,352,851; 3,485,819; etc., and the compounds wherein $R_1$ is methoxy are disclosed in various references including U.S. Pat. No. 3,954,731; British Pat. No. 1,339,007; etc.

The piperazindione acid chloride of formula III is prepared by reacting a hydrazine of the formula

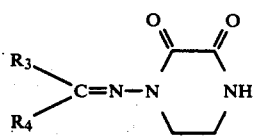
(VI)

with hydrogen in the presence of Lindar catalyst to yield the piperazindione of the formula (VII)

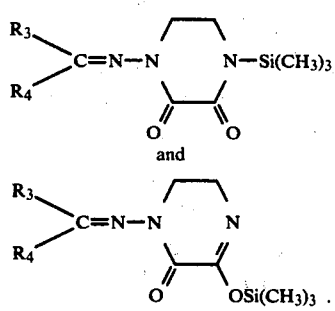

The compound of formula VII can be treated with phosgene to yield the acid chloride of formula III directly. Alternatively, the compound of formula VII is treated with a silylating agent such as trimethylsilyl chloride or N-methyl-O-trimethylsilyl chloride or N-methyl-O-trimethylsilyltrifluoroacetamide to yield a mixture of (VIII)

[structures VIII shown]
and
[second structure]

This mixture is then treated with phosgene to yield the acid chloride of formula III.

The intermediate of formula VI can be prepared according to the following reaction sequence. An aldehyde or ketone of the formula

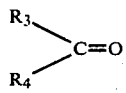

is reacted with a hydrazine of the formula

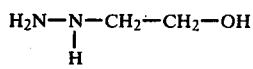 (XI)

to yield the compound of the formula

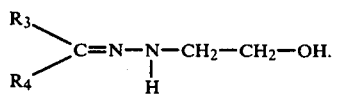 (XII)

The intermediate of formula XII is treated with propylene oxide and oxalic acid ethyl ester chloride, i.e.

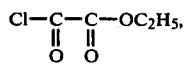

to yield the compound of the formula

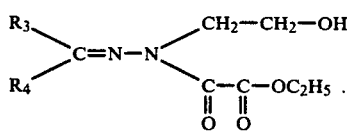 (XIII)

The intermediate of formula XIII is then treated with methylsulfonyl chloride to yield the compound of the formula

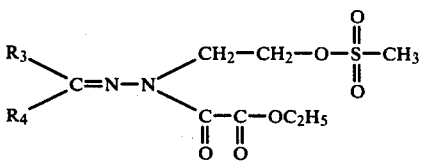 (XIV)

which is then treated in the presence of a crown ether with a lithium halide or sodium halide, preferably lithium bromide, to yield the compound of the formula

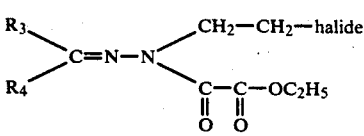 (XV)

Treatment of the compound of formula XV with an azide such as lithium azide, sodium azide, or tetramethylguanidinium azide yields the intermediate of formula VI.

The compounds of formula I can also be prepared by acylating a 6-amino penicillanic acid ester of formula IV with a compound of the formula

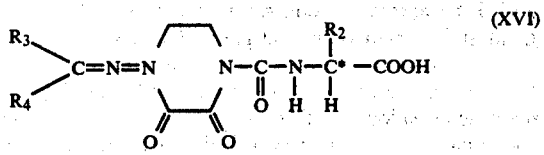

(XVI)

to yield the compounds of formula I in their ester form, i.e. R is t-butyl, benzyl, p-methoxybenzyl, p-nitrobenzyl, diphenylmethyl, 2,2,2-trichloroethyl, or trimethylsilyl. The ester protecting group can then be removed according to methods known in the art to yield the corresponding free acid compounds.

This acylation reaction can be performed directly with the acid of formula XVI by use of a coupling agent such as dicyclohexylcarbodiimide. Alternatively the acid compound of formula XVI can be converted to an activated derivative such as the acid chloride or bromide, an anhydride or mixed anhydride, or an activated ester formed according to methods known in the art.

The acid of formula XVI is prepared by reacting an α-amino acid of the formula

(XVII)

wherein E is hydrogen or a protecting group such as diphenylmethyl or p-nitrobenzyl, with the acid chloride of formula III. The protecting group can then be removed to yield the acid of formula XVI.

Also, when E is p-nitrobenzyl the resulting ester of formula XVI can be employed to directly acylate a desmethoxy 6-aminopenicillanic acid ester of formula IV (i.e. $R_1$ is hydrogen) and yield the corresponding desmethoxy compound of formula I.

The compounds of formula I wherein R is sodium or potassium are prepared by reacting the corresponding free acid of formula I with the appropriate salt forming reactant.

The compounds of formula I wherein R is

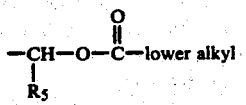

can be obtained by treating the corresponding free acid of formula I with one or two moles of a compound of the formula

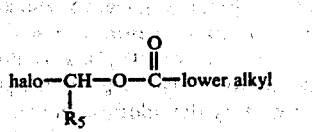

(XVIII)

wherein halo is chlorine or bromine in an inert solvent such as dimethylformamide at or below ambient temperature.

Similarly, the compounds of formula I wherein R is

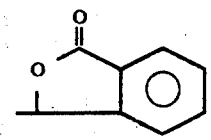

are prepared by treating the free acid compound of formula I with a compound of the formula

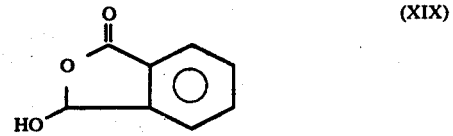

(XIX)

as taught by Ferres et al. in U.S. Pat. No. 3,860,579.

The compounds of formula I wherein $R_2$ is other than hydrogen are optically active due to the presence of an asymmetric carbon atom represented as C* in the preceding formulas. By selection of the appropriate starting material it is possible to obtain the compounds of formula I as a mixture of optically active isomers or isolated as a single isomer. The various optical isomers as well as their mixtures are within the scope of this invention.

Also, the compounds of formula I and the various intermediates wherein $R_2$ is 2-amino-4-thiazolyl are tautomeric and can be structurally represented as

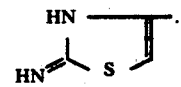

Though the 2-amino-4-thiazolyl form is being used throughout this application, both forms are within the scope of this invention.

Preferred compounds of this invention are those of formula I wherein R is hydrogen, sodium or potassium; $R_1$ is hydrogen; $R_2$ is phenyl, 4-hydroxyphenyl, 2-thienyl, 3-thienyl, 2-furyl, 3-furyl, or 2-amino-4-thiazolyl; $R_3$ is methyl, phenyl, 2-thienyl, or 2-furyl; and $R_4$ is hydrogen or methyl.

Most preferred are the above compounds wherein $R_3$ is phenyl and $R_4$ is hydrogen.

The compounds of formula I wherein R is hydrogen, sodium, potassium, —CH$_2$—O—lower alkyl,

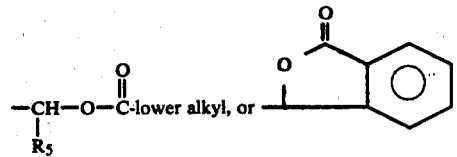

useful antibacterial agents possessing activity against various gram-positive and gram-negative organisms such as Staphylococcus aureus, Escherichia coli, Enterobacter cloacae, Klebsiella pneumoniae, Klebsiella aerogenes, Proteus rettgeri, Proteus vulgarius, Proteus mirabilis, Serratia marcescens, Salmonella typhosa, Shigella sonnei, Citrobacter freundii, Pseudomonas aeruginosa, etc. They may be used as antibacterial agents to combat infections due to organisms such as those named above, and in general may be utilized in a manner similar to other penicillins. For example, a compound of formula I or a physiologically acceptable salt thereof may be used in various animal species in an amount of about 1 to 100 mg./kg., daily in oral or parenteral form, in single or two to four divided doses to treat infections of bacterial origin, e.g., 5.0 mg./kg. in mice.

Up to about 600 mg. of an acid compound of formula I or a physiologically acceptable salt thereof may be incorporated in an oral dosage form such as tablets, capsules or elixirs or in an injectable form in a sterile aqueous vehicle prepared according to conventional pharmaceutical practice.

Illustrative process details are provided in the examples for the various reactions. All temperatures are on the centigrade scale.

EXAMPLE 1

6β-[[D-[[[2,3-Dioxo-4-[(phenylmethylene)amino]-1-piperazinyl]carbonyl]amino]phenylacetyl]amino]-3,3-dimethyl-7-oxo-4-thia-1-azabicyclo[3.2.0]heptane-2-carboxylic acid (a) [1-(2-Hydroxyethyl)-2-(phenylmethylene)hydrazino]oxoacetic acid, ethyl ester 8.2 g. of 2-[2-(phenylmethylene)hydrazino]ethanol are dissolved in 50 ml. of tetrahydrofuran. 5.6 g. of propylene oxide are added and then 7.5 g. (10% excess) of chlorooxoacetic acid ethyl ester are added dropwise at 0°. After three hours, the reaction mixture is concentrated in vacuo to yield a yellow oil which crystallizes after the addition of a small amount of toluene and overnight refrigeration. This material is filtered under suction and the residue is washed with petroleum ether to yield a light yellow powder. Recrystallization from carbon tetrachloride yields 7.6 g. of white crystalline [1-(2-hydroxyethyl)-2-(phenylmethylene)hydrazino]oxoacetic acid, ethyl ester; m.p. 96°–98°.

(b) [1-[2-[(Methylsulfonyl)oxy]ethyl]-2-(phenylmethylene)hydrazino]oxoacetic acid, ethyl ester 26.4 g. of the ethyl ester product from part (a) and 10 g. of triethylamine are dissolved in 200 ml. of methylene chloride. 11.4 g. of methylsulfonyl chloride dissolved in a small amount of methylene chloride are added dropwise at −20°. After two hours, 300 ml. of water are added to the reaction solution and this mixture is stirred for 10 minutes. The organic phase is dried (Na₂SO₄) and, after distilling off the solvent, a colorless oil is obtained which crystallizes upon scratching. Recrystallization from ethanol yields as a white powder [1-[2-[(methylsulfonyl)oxy]ethyl]-2-(phenylmethylene)hydrazino]oxoacetic acid, ethyl ester; m.p. 93°–95°.

(c) [1-(2-Bromoethyl)-2-(phenylmethylene) hydrazino]oxoacetic acid, ethyl ester 3.4 g. of the ethyl ester product from part (b) are dissolved in 100 ml. of acetone. 1.3 g. (50% excess) of lithium bromide and 0.1 g. of 18-Crown-6 (1,4,7,10,13,16-hexaoxacyclooctadecane) are added and the mixture is stirred for three hours at 50°. After the reaction has been completed as determined by TLC, the solvent is distilled off and the reaction mixture is taken up in 50 ml. of methylene chloride and shaken with 50 ml. of water. The organic phase is dried and concentrated to yield the crude product as an oil which, after scratching, crystallizes in several hours. Recrystallization from isopropanol yields purified [1-(2-bromoethyl)-2-(phenylmethylene)hydrazino]oxoacetic acid, ethyl ester; m.p. 56°–57°.

(d) [1-(2-Azidoethyl)-2-(phenylmethylene)hydrazino]oxoacetic acid, ethyl ester 11 g. of the ethyl ester product from part (c) are added to acetone along with 5.7 g. of tetramethylguanidinium azide and 0.05 g. of 18-Crown-6. The mixture is refluxed for eight hours. After distilling off the solvent, the reaction mixture is stirred with 50 ml. of methylene chloride. The organic phase, after drying and concentrating, leaves an oil which crystallizes in the form of white crystals upon the addition of a small amount of isopropanol to yield [1-(2-azidoethyl)-2-(phenylmethylene)hydrazino]oxoacetic acid, ethyl ester; m.p. 59°–61°.

(e) 1-[(Phenylmethylene)amino]-2,3-piperazinedione 2 g. of the ethyl ester product from part (d) are dissolved in 100 ml. of ethanol. 0.5 g. of Lindlar catalyst are added and the reaction mixture is stirred for four hours at room temperature under two atmospheres of hydrogen. At intervals the reaction mixture is filtered. After completion of the slow absorption of hydrogen, the reaction solution is flooded with nitrogen and then heated to a boil. This mixture is filtered while hot and after cooling 1 g. of crude product is obtained from the filtrate. Recrystallization from water yields as white crystals purified 1-[(phenylmethylene)amino]-2,3-piperazinedione; m.p. 229°–231°.

(f) 1-[(Phenylmethylene)amino]-4-(trimethylsilyl)-2,3-piperazinedione 2.1 g. of the piperazinedione product from part (e) are suspended in 50 ml. of acetonitrile. 1 g. of N-methyl-O-trimethylsilyltrifluoroacetamide are added and the mixture is refluxed for one hour. A clear solution forms and upon cooling to −10° there is obtained a thick white precipitate. NMR analysis of the precipitate indicates that it contains 1-[(phenylmethylene)amino]-4-(trimethylsilyl)-2,3-piperazinedione as the major product and about 25% by weight of 5,6-dihydro-1-[(phenylmethylene)amino]-3-[(trimethylsilyl)oxo]-2-(1H)-pyrazinone. The precipitate is filtered under suction, washed with petroleum ether, and dried under nitrogen; m.p. 190°–191°.

(g) 2,3-Dioxo-4-[(phenylmethylene)amino]-1-piperazinecarbonyl chloride 4.2 g. of the mixture obtained from part (f) are dissolved in 50 ml. of methylene chloride and a solution of 40 mM of phosgene in methylene chloride is added dropwise at 0°. Over a period of four hours a thick precipitate forms. To ensure a complete reaction, the mixture is allowed to stand overnight under refrigeration. The mixture is then filtered and the residue is dried at 40° under a vacuum to yield as a white powder 5.9 g. of 2,3-dioxo-4-[(phenylmethylene)amino]-1-piperazinecarbonyl chloride; m.p. 185° (dec.).

(h) 6β-[[D-[[[2,3-Dioxo-4-[(phenylmethylene)amino]-1-piperazinyl]carbonyl]amino]phenylacetyl]amino]-3,3-dimethyl-7-oxo-4-thia-1-azabicyclo[3.2.0]heptane-2-carboxylic acid 1.74 g. of ampicillin (i.e. 6-[D-(2-amino-2-phenylacetamido)]-3,3-dimethyl-7-oxo-4-thia-1-azabicyclo[3.2.0]heptane-2-carboxylic acid) is dissolved in 50 ml. of absolute acetonitrile with the aid of the addition of 2 g. of bistrimethylsilyl acetamide. The solution is cooled to 0° and 2 g. of propylene oxide are added followed by the addition in small portions of 1.5 g. of 2,3-dioxo-4-[(phenylmethylene)amino]-1-piperazinecarbonyl chloride. After stirring for four hours, a clear solution is obtained. This solution is allowed to come to room temperature, 10 ml. of methanol are added, and the mixture is stirred for an additional thirty minutes. The reaction mixture is then concentrated and the oily residue is treated with ethyl acetate and water. The organic phase is washed with 2 N phosphoric acid solution and then twice with water, dried, and concentrated crystallizing 6β-[[D-[[[2,3-dioxo-4-[(phenylmethylene)amino]-1-piperazinyl]carbonyl]amino]phenylacetyl]amino]-3,3-dimethyl-7-oxo-4-thia-1-azabicyclo[3.2.0]heptane-2-carboxylic acid; m.p. 161° (dec.). An additional fraction of product is obtained by adding diisopropyl ether to the mother liquor and precipitating from tetrahydrofuran; m.p. 165°–167°.

EXAMPLE 2

6β-[[D-[[[2,3-Dioxo-4-[(phenylmethylene)amino]-1-piperazinyl]carbonyl]amino]phenylacetyl]amino]-3,3-dimethyl-7-oxo-4-thia-1-azabicyclo[3.2.0]heptane-2-carboxylic acid, sodium salt 400 mg. of the acid product from Example 1 are dissolved in 5 ml. of tetrahydrofuran and 2.8 ml. of 0.2 N sodium 2-ethyl hexanoate solution are added. After the addition of 3 ml. of isopropyl ether, the reaction mixture is stirred for twenty minutes and the precipitate is filtered under suction to yield as a beige powder 6β-[[D-[[[2,3-dioxo-4-[(phenylmethylene)amino]-1-piperazinyl]carbonyl]amino]phenylacetyl]amino]-3,3-dimethyl-7-oxo-4-thia-1-azabicyclo[3.2.0]heptane-2-carboxylic acid sodium salt; m.p. 183°.

Similarly, by employing potassium ethyl hexanoate solution one obtains the corresponding potassium salt.

EXAMPLES 3–25

Following the procedure of Example 1 but employing the α-amino penicillanic acid shown in Col. I and the piperazinecarbonyl chloride shown in Col. II, one obtains the product shown in Col. III.

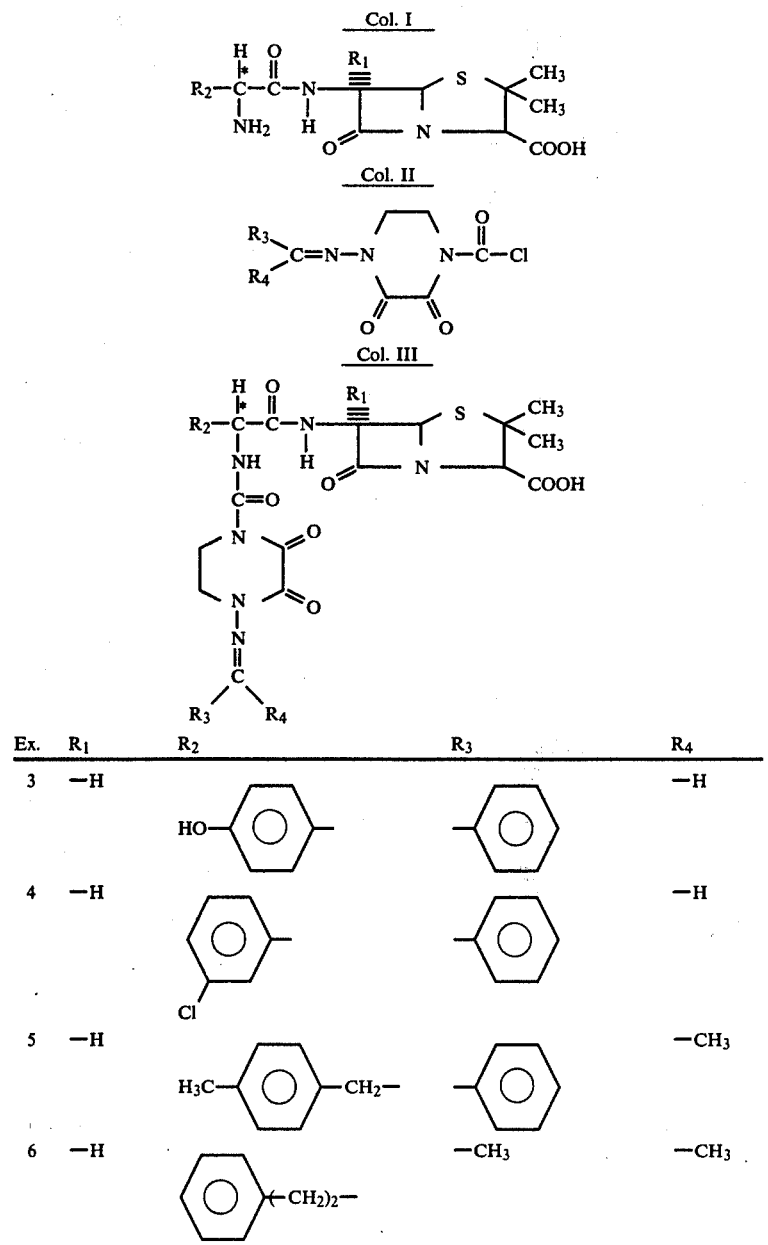

-continued
| | | | | |
|---|---|---|---|---|
| 7 | —H | 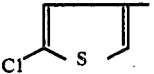 | —CH$_2$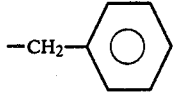 | —H |
| 8 | —OCH$_3$ |  | 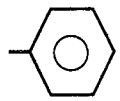 | —H |
| 9 | —H | 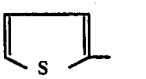 | 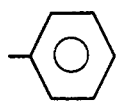 | —H |
| 10 | —H | 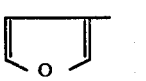 | 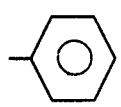 | —H |
| 11 | —H | 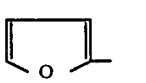 | 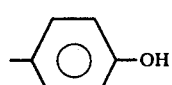 | —H |
| 12 | —OCH$_3$ |  | —CH$_3$ | —H |
| 13 | —H | 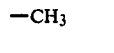 | 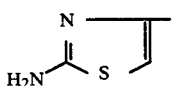 | —H |
| 14 | —H | 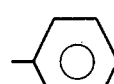 | -t-C$_4$H$_9$ | —H |
| 15 | —H | 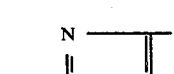 | 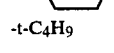 | —H |
| 16 | —H | 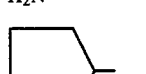 | 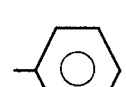 | —H |
| 17 | —H | 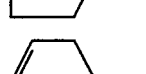 | 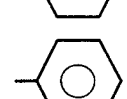 | —H |
| 18 | —H | 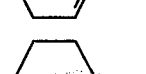 | 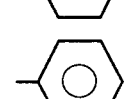 | —CH$_3$ |
| 19 | —H | 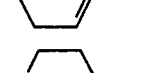 | 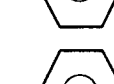 | —H |
| 20 | —H | 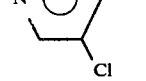 |  | —H |
| 21 | —H | 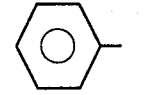 | 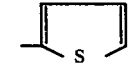 | —CH$_3$ |
| 22 | OCH$_3$ | 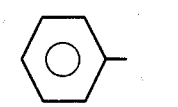 | 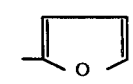 | —H |

-continued

| | | | |
|---|---|---|---|
| 23 | —H | H₅C₂O-⟨phenyl⟩- / ⟨phenyl⟩- | —C₂H₅ |
| 24 | —H | 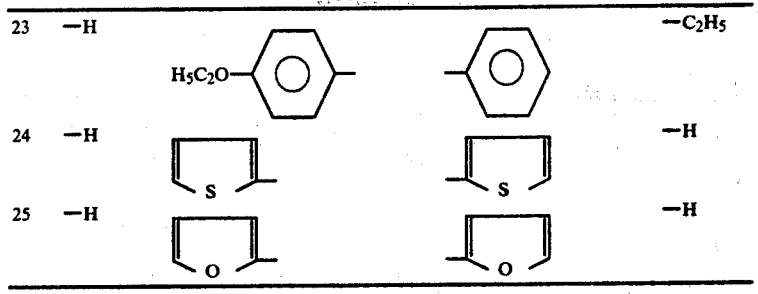 (thiophene / thiophene) | —H |
| 25 | —H | (furan / furan) | —H |

The compounds of Examples 3 to 25 are obtained in the D- or L- isomeric form or as a mixture of the D- and L- isomers depending upon the optical activity of the starting penicillin shown in Col. I.

The final products of Examples 3 to 25 can be converted to the sodium or potassium salt by following the procedure of Example 2.

Also, the penicillanic acid products of Examples 1 and 3 to 25 can be converted to various ester forms as set forth in the specification.

EXAMPLE 26

6β-[[D-[[[2,3-Dioxo-4-[(phenylmethylene)amino]-1-piperazinyl]carbonyl]amino]phenylacetyl]-amino]-3,3-dimethyl-7-oxo-4-thia-1-azabicyclo[3.2.0]heptane-2-carboxylic acid The product of Example 1 can also be prepared by the following procedure.

(a) D-α-[[[2,3-Dioxo-4-[(phenylmethylene)amino]-1-piperazinyl]carbonyl]amino]phenylacetic acid 0.75 g. of D-phenylglycine are dissolved in 50 ml. of absolute acetonitrile with the aid of 1 g. of bistrimethylsilyl acetamide. The solution is cooled to 0°, 1 g. of propylene oxide are added followed by the addition in small amounts of 1.4 g. of 2,3-dioxo-4-[(phenylmethylene)amino]-1-piperazinecarbonyl chloride, from Example 1 (g). After three hours a clear solution is obtained to which 5 ml. of methanol are added. The resulting solution is stirred for thirty minutes. The solvent is then distilled off and the hot residue is taken up in a small amount of methyl ethyl ketone. A small amount of insoluble material is removed by filtration and the filtrate is permitted to cool yielding as a precipitated white powder D-α-[[[2,3-dioxo-4-[(phenylmethylene]amino]-1-piperazinyl]carbonyl]amino]phenylacetic acid; m.p. 170°–173°.

(b) 6β-[[D-[[[2,3-Dioxo-4-[(phenylmethylene)amino]-1-piperazinyl]carbonyl]amino]phenylacetyl]amino]-3,3-dimethyl-7-oxo-4-thia-1-azabicyclo[3.2.0]heptane-2-carboxylic acid 1.81 g. of the phenylacetic acid product from part (a) are dissolved in 50 ml. of tetrahydrofuran. 0.5 g. of N-methylmorpholine are added and the mixture is cooled to −10°. 0.7 g. of chloroformic acid isobutyl ester dissolved in 20 ml. of tetrahydrofuran are added dropwise to the cooled solution. After stirring for thirty minutes, the resulting solution is added dropwise to a solution of 6-aminopenicillanic acid (6-APA) trimethylsilyl ester in 50 ml. of acetonitrile. The resulting reaction mixture is stirred for four hours at 0°. After the addition of 10 ml. of methanol, the solvent is distilled off. The residue is worked up as in Example 1(h) to yield as a white powder 6β-[[D-[[[2,3-dioxo-4-[(phenylmethylene)amino]-1-piperazinyl]carbonyl]amino]phenylacetyl]amino]-3,3-dimethyl-7-oxo-4-thia-1-azabicyclo[3.2.0]heptane-2-carboxylic acid; m.p. 165°.

EXAMPLES 27–47

Following the procedure of Example 26 but employing the α-amino acid shown in Col. I and the piperazinecarbonyl chloride shown in Col. II, one obtains the intermediate shown in Col. III. This intermediate is then converted to an activated form and reacted with 6-aminopenicillanic acid ester shown in Col. IV to yield after removal of the ester group the product shown in Col. V.

Col. I $$R_2-\overset{H}{\underset{NH_2}{C^*}}-COOH$$

Col. II

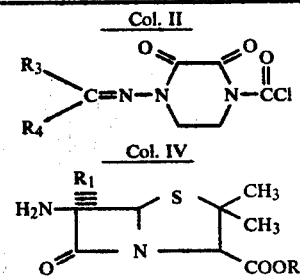

Col. III

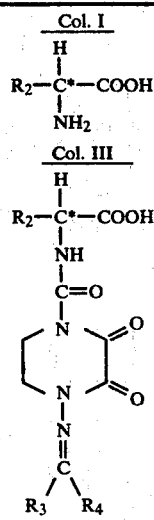

Col. IV $$H_2N-\overset{R_1}{\underset{O}{\rlap{\,\,\,\,\,\,}}}\overset{S}{\underset{N}{\rlap{\,\,}}}\overset{CH_3}{\underset{COOR}{\rlap{\,\,}}}$$

-continued

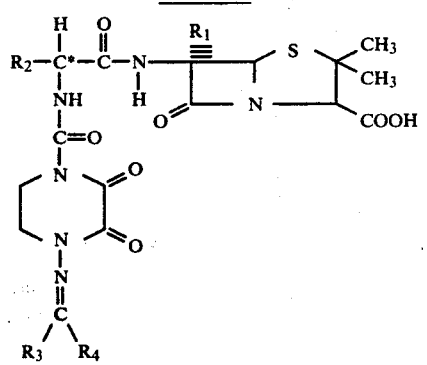

| Ex. | $R_1$ | R | $R_2$ | $R_3$ | $R_4$ |
|---|---|---|---|---|---|
| 27 | —H | —Si(CH$_3$)$_3$ | 4-HO-C$_6$H$_4$— | C$_6$H$_5$— | —H |
| 28 | —H | —Si(CH$_3$)$_3$ | 2-furyl | C$_6$H$_5$— | —H |
| 29 | —OCH$_3$ | —CH$_2$-C$_6$H$_4$-NO$_2$ | 2-thienyl | C$_6$H$_5$— | —CH$_3$ |
| 30 | —H | —Si(CH$_3$)$_3$ | 2-thienyl | C$_6$H$_5$— | —H |
| 31 | —H | —CH$_2$CCl$_3$ | 2-furyl | C$_6$H$_5$— | —H |
| 32 | —H | —Si(CH$_3$)$_3$ | 5-Cl-2-furyl | 4-HO-C$_6$H$_4$— | —H |
| 33 | —H | —CH(C$_6$H$_5$)$_2$ | C$_6$H$_5$— | C$_6$H$_5$— | —H |
| 34 | —OCH$_3$ | —CH$_2$-C$_6$H$_5$ | 2-thienyl | —CH$_3$ | —CH$_3$ |
| 35 | —H | —Si(CH$_3$)$_3$ | H$_2$N-C(=N)-S-CH=CH— | C$_6$H$_5$— | —H |
| 36 | —H | —Si(CH$_3$)$_3$ | C$_6$H$_5$— | 2-thienyl | —H |
| 37 | —H | —Si(CH$_3$)$_3$ | C$_6$H$_5$— | 2-furyl | —H |
| 38 | —H | —CH$_2$CCl$_3$ | C$_6$H$_5$— | 3-CH$_3$-2-thienyl | —CH$_3$ |

| | | | | | |
|---|---|---|---|---|---|
| 39 | —H | —Si(CH₃)₃ | HO—⟨phenyl⟩— | ⟨thiophene⟩ | —H |
| 40 | —H | —Si(CH₃)₃ | ⟨thiophene-S⟩ | ⟨thiophene-S⟩ | —H |
| 41 | —H | —Si(CH₃)₃ | ⟨thiophene-S⟩ | ⟨thiophene-S⟩ | —H |
| 42 | —H | —Si(CH₃)₃ | ⟨thiophene-S⟩ | ⟨thiophene-S⟩ | —CH₃ |
| 43 | —H | —CH₂—⟨phenyl⟩—OCH₃ | ⟨furan-O⟩ | ⟨thiophene-S⟩ | —H |
| 44 | —H | —Si(CH₃)₃ | ⟨phenyl⟩ | —CH₂—⟨phenyl⟩ | —H |
| 45 | —H | —Si(CH₃)₃ | ⟨phenyl⟩ | —CH₂—⟨phenyl⟩ | —H |
| 46 | —H | —Si(CH₃)₃ | ⟨phenyl⟩ | ⟨phenyl-Cl⟩ | —CH₃ |
| 47 | —H | —Si(CH₃)₃ | ⟨phenyl⟩ | —C₂H₅ | —H |

The final products of Examples 27 to 47 are obtained in the D- or L- isomeric form or as a mixture of the D- and L- isomers depending upon the optical activity of the α-amino acid starting material of Col. I.

The penicillanic acid products of Examples 27 to 47 can be converted to the sodium or potassium salt form according to the procedure of Example 2.

Also, the penicillanic acid products of Examples 27 to 47 can be converted to various ester forms as set forth in the specification.

What is claimed is:

1. A compound of the formula:

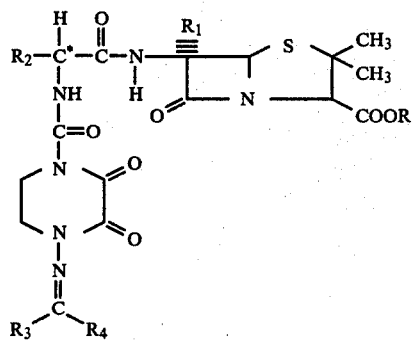

wherein R is hydrogen, sodium, potassium, t-butyl, benzyl, p-methoxybenzyl, p-nitrobenzyl, diphenylmethyl, 2,2,2-trichloroethyl, trimethylsilyl, —CH₂—O—lower alkyl,

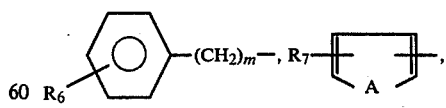

$R_1$ is in the α-configuration and is hydrogen or methoxy; $R_2$ is hydrogen, lower alkyl, cycloalkyl, cycloalkenyl, cycloalkadienyl,

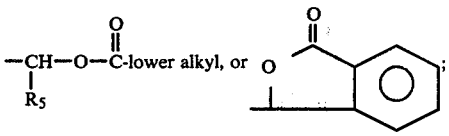

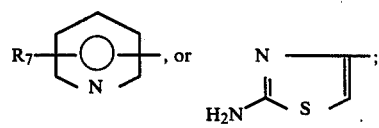

$R_3$ is lower alkyl,

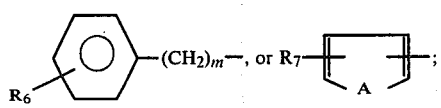

$R_4$ is hydrogen or lower alkyl; $R_5$ is hydrogen or lower alkyl; $R_6$ is hydrogen, methyl, ethyl, methoxy, ethoxy, hydroxy, Cl or Br; m is zero, one or two; A is O or S; and $R_7$ is hydrogen, methyl, ethyl, Cl, or Br.

2. The compound of claim 1 wherein R is hydrogen, sodium, or potassium; $R_1$ is hydrogen; $R_2$ is phenyl, 4-hydroxyphenyl, 2-thienyl, 3-thienyl, 2-furyl, 3-furyl, or 2-amino-4-thiazolyl; $R_3$ is methyl, phenyl, 2-thienyl or 2-furyl; and $R_4$ is hydrogen or methyl.

3. The compound of claim 2 wherein $R_3$ is phenyl and $R_4$ is hydrogen.

4. The compound of claim 3 wherein $R_2$ is phenyl.

5. The compound of claim 4, 6β-[[D-[[[2,3-dioxo-4-[(phenylmethylene)amino]-1-piperazinyl]carbonyl-]amino]phenylacetyl]amino]-3,3-dimethyl-7-oxo-4-thia-1-azabicyclo[3.2.0]heptane-2-carboxylic acid.

6. The sodium slat of the compound of claim 5.

7. An antibacterial pharmaceutical composition comprising a pharmaceutically acceptable carrier and one or more antibacterially active compounds of the formula:

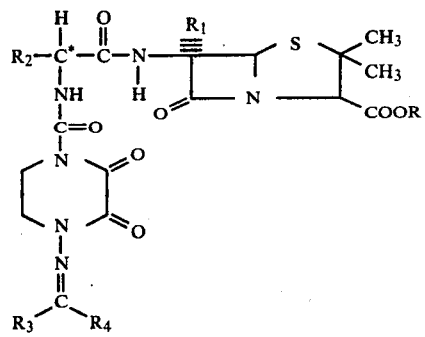

wherein R is hydrogen, sodium, potassium; —CH$_2$—O— lower alkyl,

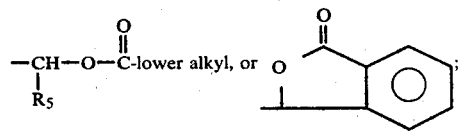

and $R_1$, $R_2$, $R_3$, $R_4$, and $R_5$ are as defined in claim 1.

8. The method of treating bacterial infections in mammals which comprises administering an effective amount of the composition of claim 7.

* * * * *